United States Patent [19]

Cilento et al.

[11] Patent Number: 4,773,409
[45] Date of Patent: Sep. 27, 1988

[54] WOUND DRESSING

[75] Inventors: Rodolfo D. Cilento, North Brunswick; Frank M. Freeman, Lawrenceville, both of N.J.

[73] Assignee: E. R. Squibb & Sons, Inc., Princeton, N.J.

[21] Appl. No.: 778,036

[22] Filed: Sep. 20, 1985

[51] Int. Cl.$^4$ ............................................. D61L 15/00
[52] U.S. Cl. .................................... 128/156; 128/155; 604/358; 428/314.4; 428/317.1
[58] Field of Search .............................. 128/155, 156; 428/305.5, 317.1, 317.3, 314.4, 314.8; 521/159; 604/368, 369, 374, 375, 897

[56] References Cited

U.S. PATENT DOCUMENTS

| | | | |
|---|---|---|---|
| 3,004,934 | 10/1961 | Desmann et al. | 260/2.5 |
| 3,075,930 | 1/1963 | Stewart et al. | 260/2.5 |
| 3,113,568 | 12/1963 | Robins | 128/156 |
| 3,121,021 | 2/1964 | Copeland | 117/122 |
| 3,157,178 | 11/1964 | Bentov | 128/156 |
| 3,339,546 | 9/1967 | Chen | 128/156 |
| 3,441,523 | 4/1969 | Dwyer et al. | 260/2.5 |
| 3,487,832 | 1/1970 | Spence | 128/156 |
| 3,547,753 | 12/1970 | Sutton | 161/160 |
| 3,566,871 | 3/1971 | Richter et al. | 128/296 |
| 3,586,648 | 6/1971 | Sambeth et al. | 260/2.5 |
| 3,648,692 | 3/1972 | Wheeler | 128/156 |
| 3,665,918 | 5/1972 | Lindquist et al. | 128/156 |
| 3,713,445 | 1/1973 | Marsan | 128/283 |
| 3,753,933 | 8/1973 | Olstowski et al. | 260/2.5 AE |
| 3,949,742 | 4/1976 | Nowakowski | 128/155 |
| 3,972,328 | 8/1976 | Chen | 128/156 |
| 3,975,567 | 8/1976 | Lock | 428/315 |
| 3,978,855 | 9/1976 | McRae et al. | 128/156 |
| 4,000,028 | 12/1976 | Hoey | 156/79 |
| 4,156,759 | 5/1979 | Hestettler | 521/102 |
| 4,197,372 | 4/1980 | Hestettler | 521/109 |
| 4,233,969 | 11/1980 | Lock et al. | 128/156 |
| 4,327,195 | 4/1982 | Clora et al. | 521/102 |
| 4,341,207 | 7/1982 | Steer et al. | 128/155 |
| 4,374,208 | 2/1983 | Fallows et al. | 521/109 |
| 4,394,930 | 7/1983 | Korpman | 220/444 |
| 4,427,737 | 1/1984 | Cilento et al. | 428/315.7 |
| 4,538,603 | 9/1985 | Pawelchak et al. | 128/156 |

FOREIGN PATENT DOCUMENTS

| | | |
|---|---|---|
| 41934 | 9/1981 | European Pat. Off. . |
| 92999 | 7/1982 | European Pat. Off. . |
| 0139942 | 1/1980 | German Democratic Rep. ........ 128/155 |
| 1538809 | 1/1979 | United Kingdom . |
| 1550614 | 8/1979 | United Kingdom . |

OTHER PUBLICATIONS

Kirk-Othmer, Enc. of Chem. Tech., 3rd Ed., (1979), vol. 11, pp. 87-89, vol. 23, pp. 576-608.
Skeist, Handbook of Adhesives, 2nd Ed., pp. 548-552.

Primary Examiner—Richard J. Apley
Assistant Examiner—Paul Prebilic
Attorney, Agent, or Firm—Lawrence S. Levinson; Stephen B. Davis

[57] ABSTRACT

An occlusive wound dressing comprising a flexible closed cell polyurethane foam containing from about 5% to about 50% by weight of the foam of one or more water dispersible, water swellable, and/or water absorbing agents. A pressure sensitive microporous adhesive is applied or laminated to one surface of the foam as a continuous layer. A polymeric film or skin is laminated or formed on the opposite surface of the foam.

26 Claims, 1 Drawing Sheet

U.S. Patent
Sep. 27, 1988
4,773,409
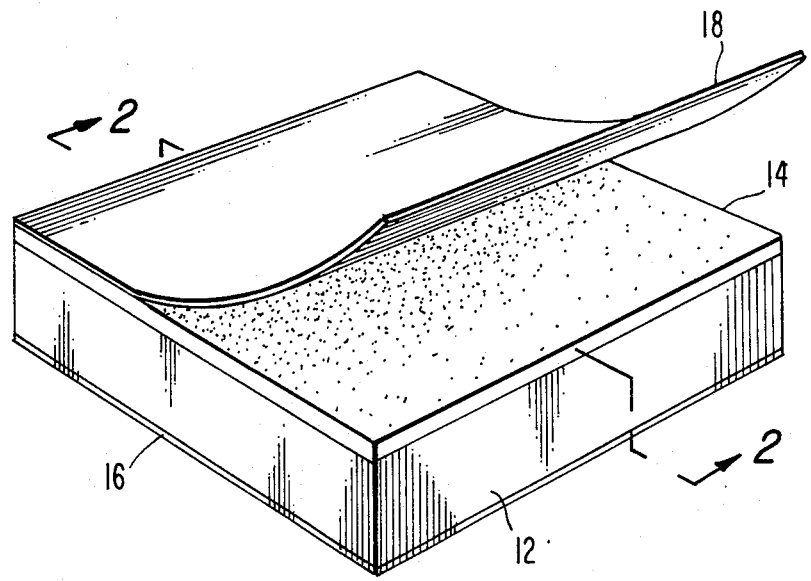
_Fig_1_
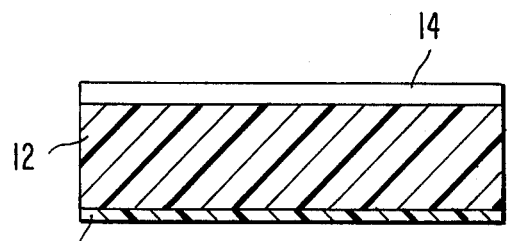
_Fig_2_

WOUND DRESSING

RELATED APPLICATION

Cilento et al. in U.S. Ser. No. 688,859 filed Jan. 4, 1985, now abandoned in favor of continuation-in-part U.S. Ser. No. 780,108 filed on Sept. 15, 1985, discloses a wound dressing including a flexible closed cell polyurethane foam layer containing within the foam network from about 10% to about 65% by weight of the foam of one or more water dispersible, water swellable, and/or water absorbing agents. A pressure sensitive adhesive is applied or laminated onto one surface of the foam in a discontinuous pattern so that portions of the foam surface are uncovered.

BACKGROUND OF THE INVENTION

Kelly et al. in British Patent No. 1,550,614 disclose an absorbent material suitable for incorporation in sanitary towels, tampons and napkins comprising an absorbent starch derivative, preferably a cross-linked starch, distributed in a flexible resilient polyurethane foam.

W. R. Grace & Co. in British Patent No. 1,538,809 disclose a hydrophilic polyurethane foam in which a cross-linked carboxymethylcellulose and other water soluble or water dispersible materials such as sodium carboxymethylcellulose are incorporated.

Chen in U.S. Pat. No. 3,972,328, Steer et al. in U.S. Pat. No. 4,341,207, and Pawelchak et al. in European Patent Application No. 92,999 and U.S. Pat. No. 4,538,603 disclose multi-layered dressings including an intermediate layer of semi-open cell polyurethane foam and an adhesive layer which contacts the wound and surrounding skin. Lindquist et al. in U.S. Pat. No. 3,665,918 disclose a surgical tape or drape consisting of compressed polyurethane foam coated with a microporous pressure sensitive adhesive.

Richter et al. in U.S. Pat. No. 3,566,871 disclose a hydrophilic polyurethane sponge for medical use in which the sponge pores contain a surfactant coating. McRae et al. in U.S. Pat. No. 3,978,855 disclose a polyurethane foam surgical dressing in which a surface of the foam is compressed and wherein the foam also contains a wetting agent. Lock in U.S. Pat. No. 3,975,567 discloses a polyurethane foam surgical dressing in which one surface is rendered lyophilic by applying pressure and heat. Lazlo in European patent application No. 41,934 disclose a wound exudate absorbent product comprising a polyurethane foam having a water-insoluble hydrophilic polymer such as cross-linked dextran incorporated within a portion of the foam cells. Marsan in U.S. Pat. No. 3,713,445 discloses an ostomy sealing ring consisting of an open cell polyurethane or polyethylene foam containing a gelatinous material such as karaya powder and glycerine. Various polyurethane foam dressings are disclosed by Robins in U.S. Pat. No. 3,113,568, Bentov in U.S. Pat. No. 3,157,178, Wheeler in U.S. Pat. No. 3,648,692, and Nowakowski in U.S. Pat. No. 3,949,742.

Cilento et al. in U.S. Pat. No. 4,427,737 disclose a breathable tape comprising a porous backing layer and a microporous adhesive layer. The adhesive layer includes a rubbery elastomer, one or more water soluble or swellable hydrocolloids, and other optionally substances and has a porosity of from about 1 to about 100 cc/sec/in$^2$. Copeland in U.S. Pat. No. 3,121,021 describes a translucent breathable surgical tape formed of a backing layer of porous, non-woven rayon fabric and a layer of microporous acrylic pressure sensitive adhesive.

SUMMARY OF THE INVENTION

This invention is directed to an occlusive wound dressing which includes a flexible closed cell polyurethane foam layer containing within the foam network from about 5% to about 50% by weight of the foam of one or more water dispersible, water swellable, and/or water absorbing agents. A pressure sensitive microporous adhesive is applied or laminated onto one surface of the foam. In use, this adhesive surface contacts the wound site and the surrounding skin. A polymeric film may be laminated to or a skin may be formed on the opposite surface of the foam so as to protect the dressing.

BRIEF DESCRIPTION OF THE DRAWINGS

FIG. 1 is an overall view of the wound dressing of this invention (greatly enlarged) including a sheet of release paper shown partially peeled away from the adhesive layer.

FIG. 2 is a front view along line 2—2 of FIG. 1 without the release paper.

DETAILED DESCRIPTION OF THE INVENTION

The occlusive dressing 10 of this invention as shown in FIGS. 1 and 2 includes a layer of closed cell polyurethane foam 12. This foam layer contains from about 5% to about 50% by weight of the foam of one or more water dispersible or water swellable agents. A pressure sensitive microporous adhesive layer 14 is coated or laminated to one surface of foam layer 12 as a continuous layer so that the entire surface of the foam is covered. The porosity of adhesive layer 14 enables wound exudate to migrate through this layer to contact the foam where it reacts with the water dispersible, water swellable, and/or water absorbing agents within the foam network.

The top surface of foam layer 12 when viewing the dressing placed on a wound is sealed so that soil and water can not penetrate into the dressing. A thin film 16 of polymeric material such as polyurethane can be laminated to the top surface of foam layer 12 or the top surface of the foam can be treated with heat and/or pressure to flame laminate skin 16 on the surface of the foam. In another procedure, the skin 16 is cast and cured on a release liner and then the foam layer 12 is cast and formed directly on the skin.

The foam layer 12 is a flexible closed cell polyurethane foam formed from a polyester or a polyether and having one or more water dispersible, water swellable, and/or water absorbing agents distributed throughout the structure of the foam. Preferably, the foam should be of a density of from about 10 pounds/cubic foot to about 50 pounds/cubic foot.

Suitable water dispersible, water swellable, and/or water absorbing agents include one or more of sodium or calcium carboxymethylcellulose, pectin, gelatin, guar gum, locust bean gum, collagen, gum karaya, water insoluble cross-linked sodium carboxymethylcellulose such as that commercially available under the trademark Aqualon or that described in U.S. Pat. No. 3,589,364 and available commercially from the Buckeye Cellulose Corp., substantially water insoluble starch-acrylonitrile graft copolymer such as that described in U.S. Pat. No. 3,661,815 and that available commercially under the trademark Water Lock from the Grain Processing Corp., and substantially water insoluble crosslinked dextran such as that commercially available under the trademark Sephadex.

Preferred water dispersible, water swellable, and/or water absorbing agents are as follows. One or more of pectin, gelatin, and sodium carboxylmethylcellulose together at from about 10% to about 50% by weight of the foam and particularly an equal weight blend of pectin, gelatin, and sodium carboxymethylcellulose together at about 30% by weight of the foam. A water insoluble starch-acrylonitrile graft copolymer at from about 5% to about 22% by weight of the foam and most preferably at about 12% by weight of the foam. A mixture of from about 2 parts by weight of one or more of pectin, gelatin, and sodium carboxymethylcellulose, most preferably an equal weight blend of pectin, gelatin and sodium carboxymethylcellulose, and about one part by weight of a water insoluble starch-acrylonitrile graft copolymer. This mixture is present at from about 12% to about 48% by weight of the foam with the most preferred mixture being about 5% pectin, about 5% gelatin, about 5% sodium carboxymethyl cellulose, and about 7.5% of a water insoluble starch-acrylonitrile graft copolymer by weight of the foam.

In addition, small amounts, i.e., in toto less than about 5% by weight of the foam layer, of other agents may be included with the water dispersible, water swellable and/or water absorbing agents. For example, a pharmaceutically active ingredient such as an antibiotic or antimicrobial agent, an antiseptic agent such as povidone iodine, or an antiinflammatory agent such as hydrocortisone or triamcinolone acetonide may be included. Other materials such as a deodorant, perfume agent, or antioxidant could be included. Also, substances conventionally employed in the manufacture of polyurethane foams to increase strength or flexibility can be included as long as they are safe and non-irritating to the human skin.

The flexible closed cell polyurethane foam 12 containing the water dispersible, water swellable and/or water absorbing agents plus any additional ingredients as described above can be prepared by either the conventional one-shot process or the conventional prepolymer process. In the one-shot process, a polyol, isocyanate and water are reacted substantially simultaneously with the water dispersible, water swellable and/or water absorbing agents and other ingredients suspended in the mixed reactants. In the prepolymer process, the polyol is reacted with enough polyisocyanate to form a prepolymer with isocyanate end groups plus excess isocyanate. This prepolymer mixture is then reacted with a blowing agent and a slurry of the water dispersible, water swellable, and/or water absorbing agents and other ingredients in a suitable solvent. After mixing, the resin can be dispersed by several methods. Typical methods are as an expandable liquid, as a spray of small droplets of mixed resin which adhere to surfaces and foam on these surfaces, or as a froth into which some gas has been mixed prior to exiting from the mixing head which causes the liquid mixture to froth as its pressure is decreased to atmospheric pressure. Additional materials may be used in order to form the polyurethane. For example, catalysts such as the tin catalysts, i.e., stannous octoate or dibutyl tin dilaurate, and an amine catalyst such as dimethylaminoethyl ether may be used to promote the reaction of the polyol and the isocyanate. A chemical blowing agent may be added which releases a gas due to the chemical decomposition of such blowing agent as a consequence of the heat of reaction or the external raising of the reaction temperature. Also, water may be used as a blowing agent since the isocyanate when reacted with water release carbon dioxide.

Typical polyurethane foam processes are described in more detail in Kirk-Othmer, Enc. of Chem. Tech., 3rd, (1979), Vol. 11, p 87–89 and Vol. 23, p 576–608, British Patent Nos. 1,550,614 and 1,538,809 noted above, and in U.S. Pat. Nos. 3,004,934, 3,075,930, 3,441,523, 3,586,648, 3,753,933, 4,156,759, 4,197,372, 4,327,195, and 4,374,208.

In the preferred process the polyurethane foam 12 containing the water dispersible, water swellable, and/or water absorbing agents and any other optional agents is cast onto a polymeric film 16 which had previously been cast on silicone coated release paper. Alternatively, one surface of the foam 12 can be treated with heat and pressure to form skin 16.

Pressure sensitive microporous adhesive 14 may be of an acrylic type formed as taught by Copeland in U.S. Pat. No. 3,121,021. Suitable acrylics include acrylic esters particularly those with four or more carbon atoms in the alcohol component such as n-butyl acrylate and/or 2-ethylhexyl acrylate. The acrylic adhesive may contain other comonomers such as vinyl acetate, acrylonitrile, styrene, ethyl acrylate, methyl methacrylate, $\alpha,\beta$-unsaturated carboxylic acids, esters, or half esters of unsaturated dicarboxylic acids. Terpolymers are also often used for this purpose. A discussion of pressure sensitive acrylic adhesives appears in Handbook of Adhesive, 2nd Edition, Skeist, pages 548–552.

Pressure sensitive microporous adhesive 14 may be formed from a mixture of a rubbery elastomer, one or more water dispersible agents, a tackifier, a plasticizer, and other optional ingredients. As taught by Cilento et al., in U.S. Pat. No. 4,427,737, this microporous adhesive preferably contains of from about 35% to about 50% by weight of rubbery elastomer, from about 30% to to about 60% by weight of water dispersible agents, and up to 35% by weight of one or more tackifiers, plasticizers, antioxidants, and preservatives. Preferably, the elastomer is a mixture of low and medium molecular weight polyisobutylenes, the water dispersible agent is a mixture of a sodium carboxymethylcellulose and gelatin, the tackifier is a terpene resin, and the plasticizer is mineral oil.

The acrylic or rubbery elastomer adhesive can be made microporous by employing the solvent evaporation technique described by Copeland in U.S. Pat. No. 3,121,021 and Cilento et al. in U.S. Pat. No. 4,427,737. In this procedure, the solids are dispersed in a solvent such as heptane to form a slurry. The slurry is cast onto silicone coated release paper to the desired thickness and the material is then passed through a multi-zone drying tunnel so as to evaporate off the solvent.

Alternatively, the adhesive can be made microporous by forming an aqueous emulsion of the solids, adding a surfactant or a viscosity building agent such as sodium carboxymethylcellulose and incorporating air or other gaseous bubbles into the emulsion. This emulsion is then cast onto silicone coated release paper and dried by passing through a multi-zone drying tunnel.

The pressure sensitive microporous adhesive layer including the silicone coated release paper is laminated (adhesive 14 contacting the foam) with pressure to the surface of foam 12 opposite polymeric film or skin 16. The resulting product is cut to the desired shape and packaged preferably with the release paper covering adhesive 14. At the time of use, the release paper is peeled away as shown in FIG. 1 and the wound dressing is applied to skin. If desired, the edges of the dressing may be more firmly attached to the body and prevented from curling by applying strips of a microporous adhesive tape.

Preferably, foam layer 12 will be from about 10 to about 100 mils thickness, most preferably from about 20 to about 30 mils thickness, pressure sensitive microporous adhesive 14 will be from about 1 to about 10 mils thickness, most preferably from about 2 to about 4 mils thickness, and skin or polymeric film layer 16 will be from about 0.5 to about 3 mils thickness, most preferably about 1 mils thickness.

EXAMPLE 1

Polyurethane is cast onto a sheet of silicone release paper to give a film of about 1 mils thickness.

A flexible closed cell polyurethane foam is prepared by reacting appropriate amounts of a polyether polyol such as poly(oxyethylene) glycol, an isocyanate such as 4,4'-methylenebis(phenyl isocyanate), catalysts such as stannous octoate and dimethylaminoethyl ether and water (blowing agent) with sufficient starch-acrylonitrile graft copolymer (J-500 Water Lock). The starch-acrylonitrile graft copolymer is dispersed in the polyol. The other ingredients are mixed in a suitable vessel. The two mixtures are then intermixed at high speed in an in-line mixer, poured onto the polyurethane film, and allowed to cure to give a flexible closed cell polyurethane foam of about 25 mils thickness containing about 12% starch-acrylonitrile graft copolymer by weight of the foam.

An acrylic pressure sensitive microporous adhesive is prepared by homogenizing an aqueous emulsion (52% by weight solids) of 100 g. of Gelva RA2333 (water-based pressure sensitive acrylic resin from Monsanto), adding 0.7 g. of sodium carboxymethylcellulose, and continuing the homogenation to introduce air bubbles into the emulsion. This slurry is cast onto a sheet of silicone coated release paper at a wet thickness of about 10 mils. This material is passed through a multi-zone drying tunnel with a residence time of 5 to 10 minutes. The resulting dry microporous adhesive is about 4 mils thick.

This microporous acrylic adhesive is laminated to the closed cell polyurethane foam by gently compressing the adhesive to the foam by passing through pressure rollers.

The resulting wound dressing is cut to the desired size and packaged.

EXAMPLE 2-15

Following the procedure of Example 1 but employing the following ingredients on a weight percent basis within polyurethane foam layer 12 other dressings within the scope of this invention are obtained.

| | Example | | | |
|---|---|---|---|---|
| | 2 | 3 | 4 | 5 |
| Guar gum | — | — | 15 | — |
| Locust bean gum | — | — | — | 10 |
| Pectin | 5 | 10 | — | — |
| Karaya | — | — | — | 10 |
| Gelatin | 5 | 10 | 5 | — |
| Sodium carboxymethylcellulose | 5 | 10 | 10 | — |
| Collagen | — | — | — | — |
| Cross-linked sodium carboxymethylcellulose (Aqualon R) | — | — | — | — |
| Starch-acrylonitrile graft copolymer (J-500 Water Lock) | — | — | — | — |
| Cross-linked dextran (Sephadex CM-C50) | 7.5 | — | — | — |

| | 6 | 7 | 8 | 9 | 10 |
|---|---|---|---|---|---|
| Guar gum | — | 10 | — | 10 | — |
| Locust bean gum | — | — | — | — | — |
| Pectin | — | — | — | — | 10 |
| Karaya | — | — | — | — | — |
| Gelatin | — | 10 | — | — | — |
| Sodium carboxymethylcellulose | 10 | — | — | — | 10 |
| Collagen | 10 | — | — | — | — |
| Cross-linked sodium carboxymethylcellulose (Aqualon R) | — | 15 | — | 10 | — |
| Starch-acrylonitrile graft copolymer (J-500 Water Lock) | — | — | 15 | 20 | — |
| Cross-linked dextran (Sephadex CM-C50) | — | — | — | — | 10 |

| | 11 | 12 | 13 | 14 | 15 |
|---|---|---|---|---|---|
| Guar gum | — | 7 | — | — | — |
| Locust bean gum | — | — | — | — | — |
| Pectin | — | — | 7 | 10 | 10 |
| Karaya | — | 7 | — | — | — |
| Gelatin | 5 | — | 7 | 10 | — |
| Sodium carboxymethylcellulose | — | 16 | 6 | — | 10 |
| Collagen | — | — | — | — | — |
| Cross-linked sodium carboxymethylcellulose (Aqualon R) | — | — | — | 10 | — |
| Starch-acrylonitrile graft copolymer (J-500 Water Lock) | 10 | — | — | — | 10 |
| Cross-linked dextran (Sephadex CM-C50) | 10 | — | — | — | — |

EXAMPLE 16

Following the procedure of Example 1 but substituting for the microporous acrylic adhesive a pressure sensitive adhesive of the following composition:

| | Percent by weight |
|---|---|
| Polyisobutylene (Vistanex LM-MH) | 18.0 |
| Polyisobutylene (Vistanex L-100) | 20.0 |
| Terpene resin (Piccolyte) | 20.0 |
| Butylated hydroxytoluene | 0.5 |
| Mineral oil | 8.5 |
| Sodium carboxymethylcellulose | 18.0 |
| Gelatin | 15.0 |

The above solids are dispersed in sufficient heptane to make a slurry containing 40% by weight solids. The slurry is appled via a knife-over-roller onto silicone coated release paper to a wet thickness of 10 mils. The material is then passed through a multi-zone oven with a residence time of 5–10 minutes so as to reduce the solvent content to less than 1%. The resulting dry adhesive layer is 3 mils thick and has a porosity of about 5 cc/sec/in$^2$. As the dry film emerges from the oven, it is laminated to the closed cell polyurethane foam prepared as described in Example 1 by gently compressing the adhesive to the foam by passing through pressure rollers.

The resulting wound dressing is cut to the desired size and packaged.

In a similar manner, the pressure sensitive microporous adhesive of this Example can be employed with the polyurethane foams of Examples 2 to 15.

What is claimed is:

1. An occlusive wound dressing consisting essentially of a flexible closed cell polyurethane foam having dispersed therein from about 5% to about 50% by weight of said foam of one or more water dispersible, water swellable, and/or water absorbing agents selected from the group consisting of sodium carboxymethylcellulose, calcium carboxymethylcellulose, pectin, gelatin, guar gum, locust bean gum, collagen, karaya, water insoluble cross-linked sodium carboxymethylcellulose, substantialy water insoluble starch-acrylonitrile graft copolymer, and substantially water insoluble cross-linked dextran, a thin polymeric film or a skin laminated to one surface of said foam, and a pressure sensitive microporous adhesive laminated to the other surface of said foam as a continuous layer.

2. The dressing of claim 1 wherein said foam is from about 10 to about 100 mils in thickness, said polymeric film or skin is from about 0.5 to about 3 mils in thickness, and said pressure sensitive microporous adhesive is from about 1 to about 10 mils in thickness.

3. The dressing of claim 2 wherein said microporous adhesive is an acrylic adhesive.

4. The dressing of claim 3 wherein said foam has a density of from about 10 pounds/cubic foot to about 50 pounds/cubic foot.

5. The dressing of claim 4 wherein said foam is from about 20 to about 30 mils thickness, said pressure sensitive adhesive is from about 2 to about 4 mils thickness, and said polymeric film or skin is about 1 mils thickness.

6. The dressing of claim 2 wherein said microporous adhesive comprises a mixture of a rubber elastomer, one or more water dispersible agents, a tackifier, a plasticizer, and other optional ingredients.

7. The dressing of claim 6 wherein said elastomer is present at from about 35% to about 50% by weight of said adhesive, said water dispersible agent or agents are present at from about 30% to about 60% by weight of said adhesive, and said tackifier, plasticizer, and other optional ingredients combined are present at up to 35% by weight of said adhesive.

8. The dressing of claim 7 wherein said elastomer is a mixture of low and medium molecular weight polyisobutylenes, said water dispersible agent is a mixture of sodium carboxymethylcellulose and gelatin, the tackifier is a terpene resin, and the plasticizer is mineral oil.

9. The dressing of claim 8 wherein said foam has a density of from about 10 pounds/cubic foot to about 50 pounds/cubic foot.

10. The dressing of claim 9 wherein said foam is from about 20 to about 30 mils thickness, said pressure sensitive adhesive is from about 2 to about 4 mils thickness, and said polymeric film or skin is about 1 mils thickness.

11. An occlusive wound dressing consisting essentially of a flexible closed cell polyurethane foam of from about 10 to about 100 mils thickness and a density of from about 10 pounds/cubic foot to about 50 pounds/cubic foot having distributed therein from about 10% to about 50% by weight of the foam of one or more agents selected from the group consisting of pectin, gelatin, and sodium carboxymethylcellulose, a polyurethane film or skin of from about 0.5 to about 3 mils thickness laminated to one surface of said foam, and a pressure sensitive microporous adhesive of from about 1 to about 10 mils thickness laminated to the other surface of said foam as a continuous layer.

12. The dressing of claim 11 wherein said foam is from about 20 to about 30 mils thickness, said pressure sensitive microporous adhesive is from about 2 to about 4 mils thickness, and said polyurethane film or skin is about 1 mils thickness.

13. The dressing of claim 12 wherein said pectin, gelatin, and sodium carboxymethylcellulose are present in said foam at about equal amounts on a weight percent basis.

14. The dressing of claim 13 wherein said foam contains about 30% by weight of said mixture of pectin, gelatin, and sodium carboxymethylcellulose.

15. The dressing of claim 14 wherein said pressure sensitive microporous adhesive is an acrylic adhesive.

16. The dressing of claim 14 wherein said pressure sensitive microporous adhesive is a blend of low and medium molecular weight polyisobutylenes, sodium carboxymethylcellulose, gelatin, terpene resin, and mineral oil.

17. An occlusive wound dressing consisting essentially of a flexible closed cell polyurethane foam of from about 10 to about 100 mils thickness and a density of from about 10 pounds/cubic foot to about 50 pounds/cubic foot having distributed therein from about 5% to about 22% by weight of said foam of a water insoluble starch-acrylonitrile graft copolymer, a polyurethane film or skin of from about 0.5 to about 3 mils thickness laminated to one surface of said foam, and a pressure sensitive microporous adhesive of from about 1 to about 10 mils thickness laminated to the other surface of said foam as a continuous layer.

18. The dressing of claim 17 wherein said foam is from about 20 to about 30 mils thickness, said pressure sensitive microporous adhesive is from about 2 to about 4 mils thickness, and said polyurethane film or skin is about 1 mils thickness.

19. The dressing of claim 18 wherein said foam contains about 12% by weight of a water insoluble starch-acrylonitrile graft copolymer.

20. The dressing of claim 19 wherein said pressure sensitive microporous adhesive is an acrylic adhesive.

21. The dressing of claim 19 wherein said pressure sensitive microporous adhesive is a blend of low and medium molecular weight polyisobutylenes, sodium carboxymethylcellulose, gelatin, terpene resin, and mineral oil.

22. An occlusive wound dressing consisting essentially of a flexible closed cell polyurethane foam of from about 10 to about 100 mils thickness and a density of from about 10 pounds/cubic foot to about 50 pounds/cubic foot and having distributed therein from about 12% to about 48% by weight of said foam of a mixture of from about 2 parts by weight of one or more of pectin, gelatin, and sodium carboxymethylcellulose and about 1 part by weight of a water insoluble starch-acrylonitrile graft copolymer, a polyurethane film or skin of from about 0.5 to about 3 mils thickness laminated to one surface of said foam, and a pressure sensitive microporous adhesive of from about 1 to about 10 mils thickness laminated to the other surface of said foam as a continuous layer.

23. The dressing of claim 22 wherein said foam is about 20 to about 30 mils thickness, said pressure sensitive microporous adhesive is from about 2 to about 4 mils thickness, and said polyurethane film or skin is about 1 mils thickness.

24. The dressing of claim 23 wherein said foam contains about 5% by weight of pectin, about 5% by weight of gelatin, about 5% by weight of sodium carboxymethylcellulose, and about 7.5% by weight of a water insoluble starch-acrylonitrile graft copolymer.

25. The dressing of claim 24 wherein said pressure sensitive microporous adhesive is an acrylic adhesive.

26. The dressing of claim 24 wherein said pressure sensitive microporous adhesive is a blend of low and medium molecular weight polyisobutylenes, sodium carboxymethylcellulose, gelatin, terpene resin, and mineral oil.

* * * * *